United States Patent [19]

Sorensen

[11] Patent Number: 5,132,020
[45] Date of Patent: Jul. 21, 1992

[54] SORPTION OF ALCOHOLS USING ZEOLITE BETA

[75] Inventor: Charles M. Sorensen, Wilmington, Del.

[73] Assignee: Mobil Oil Corp., Fairfax, Va.

[21] Appl. No.: 776,950

[22] Filed: Oct. 15, 1991

[51] Int. Cl.$^5$ .............................................. C02F 1/28
[52] U.S. Cl. ...................................... 210/670; 55/75; 210/673; 210/679; 210/691
[58] Field of Search ..................... 55/75; 210/670, 673, 210/679, 691

[56] References Cited

U.S. PATENT DOCUMENTS

| Re. 28,341 | 2/1975 | Wadlinger et al. | 208/120 |
|---|---|---|---|
| 3,308,069 | 3/1967 | Wadlinger et al. | 252/455 |
| 3,793,385 | 2/1974 | Bond et al. | 585/828 |

FOREIGN PATENT DOCUMENTS

WO/870559 9/1987 World Int. Prop. O. .

OTHER PUBLICATIONS

Molestone, N. B., et al., "Concentration of Alcohols by Adsorption on Silicate", J. Chem. Tech. Biotechnol. vol. 31, pp. 732-736 (1981).

Einicke, W-D., et al., "notes; Liquid-Phase Adsorption of n-Alcohol/Water Mixtures on Zeolite NaZSM-5", Journal Of Colloid And Interface Science, vol. 122, pp. 280-282 (1988).

Rabo, J. A. ed., Zeolite Chemistry And Catalysis, ACS Monograph 171, pp. 220-221, (1976).

Pitt, W. W., et al., "Recovery of Ethanol from Fermentation Broths Using Selective Sorption-Desorption, Biotechnology And Bioengineering", vol. XXV, pp. 123-131 (1983).

*Primary Examiner*—Ivars Cintins
*Attorney, Agent, or Firm*—Alexander J. McKillop; Charles J. Speciale; Lori F. Cuomo

[57] ABSTRACT

A process for the sorption of alcohols by using zeolite Beta as a sorbent. The process is useful for separating alcohols, such as isopropanol and phenol, from an aqueous solution. the process is also useful for separating alcohols from an alcohol-containing vapor stream.

18 Claims, 2 Drawing Sheets

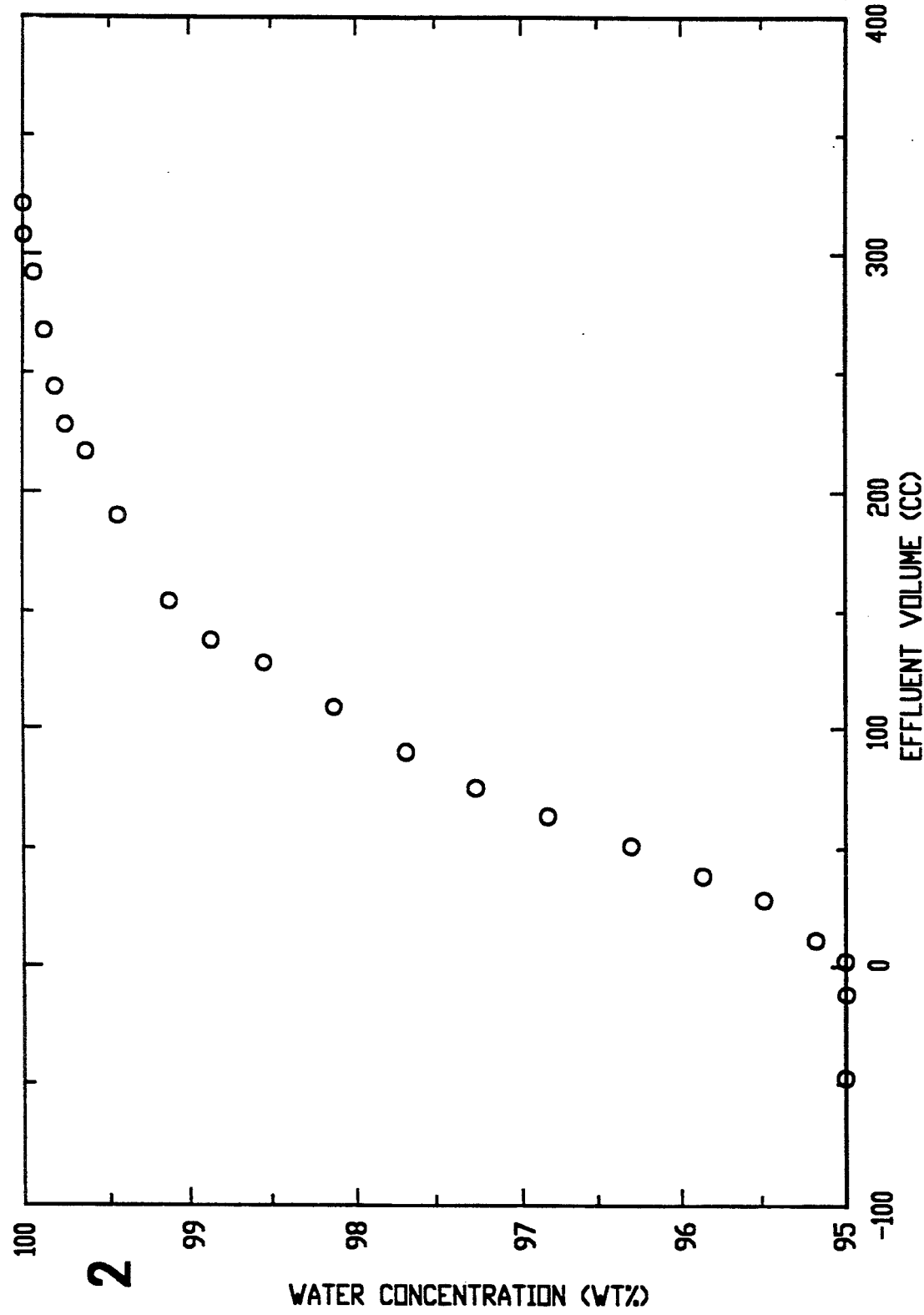

SORPTION OF ALCOHOLS USING ZEOLITE BETA

FIELD OF THE INVENTION

This application is directed to a process for the sorption of alcohols using zeolite Beta as a sorbent.

The invention also relates to a process for the separation of alcohols from an aqueous solution and further relates to a process for the separation of alcohols from an alcohol-containing vapor stream.

BACKGROUND OF THE INVENTION

Zeolite materials, both natural and synthetic, have been demonstrated to have sorption properties for various gases, vapors and liquids. Milestone et al. show the use of a high silica ZSM-5 for adsorption of ethanol and 1-butanol, Milestone, N. B. et al., *J Chem Technol. Biotechnol*, 31, No.12, 732–736 (1981).

Einicke et al. teach the use of ZSM-5 for the adsorption of ethanol, n-propanol and n-butanol from aqueous solutions, Einicke, W. D. et al., *J. Colloid Interface Sci.*, 122, No.1, 280–282 (1988). Rabo et al. discuss methanol adsorption on hydrogen mordenite and on Li-, Na-, K-, Rb-, Cs-, and Sr- and decationized X, *Zeolite Chemistry and Catalysis*, ACS Monograph 171, American Chemical Society, Washington, D.C. (1976).

Pitt et al. discuss a method for the selective sorption-desorption of ethanol using an undisclosed molecular sieve with hydrophobic properties, Pitt, W. W. et al., *Biotechnol. Bioeng.* 25, 123 (1983).

PCT Application WO 87/0559 discloses the possibility using high silica zeolites for adsorbing phenols and other toxic impurities from wastewater. The use of specific zeolites not disclosed.

Therefore, it is an object of this invention to provide an improved process for the sorption of alcohols using zeolite Beta. It is a further object of this invention to provide a process for the separation of alcohols from an aqueous solution using zeolite Beta. It is a further object of this invention to provide a wastewater treatment method.

It is a feature of this invention to provide a process for the selective sorption of isopropanol from an aqueous solution using zeolite Beta. It is a further feature of this invention to provide a process for the selective sorption of phenol from an aqueous solution using zeolite Beta. It is still a further feature of this invention to provide a process for the separation of alcohols from an alcohol-containing vapor stream.

SUMMARY OF THE INVENTION

The present invention provides a process for the sorption of alcohols by using zeolite Beta as a sorbent.

The invention therefore includes a process for the separation of alcohol from an aqueous alcohol-containing solution comprising contacting the aqueous solution with a composition comprising zeolite Beta for a sufficient time to sorb said alcohol.

The invention further includes a process for the separation of alcohol from an alcohol-containing vapor stream comprising contacting the alcohol-containing vapor stream with a composition comprising zeolite Beta for a sufficient time to sorb said alcohol.

BRIEF DESCRIPTION OF THE DRAWINGS

FIG. 2 shows the breakthrough curve for desorption of isopropanol from the bed by elution with 100% water.

DETAILED DESCRIPTION OF THE INVENTION

Figure 1:
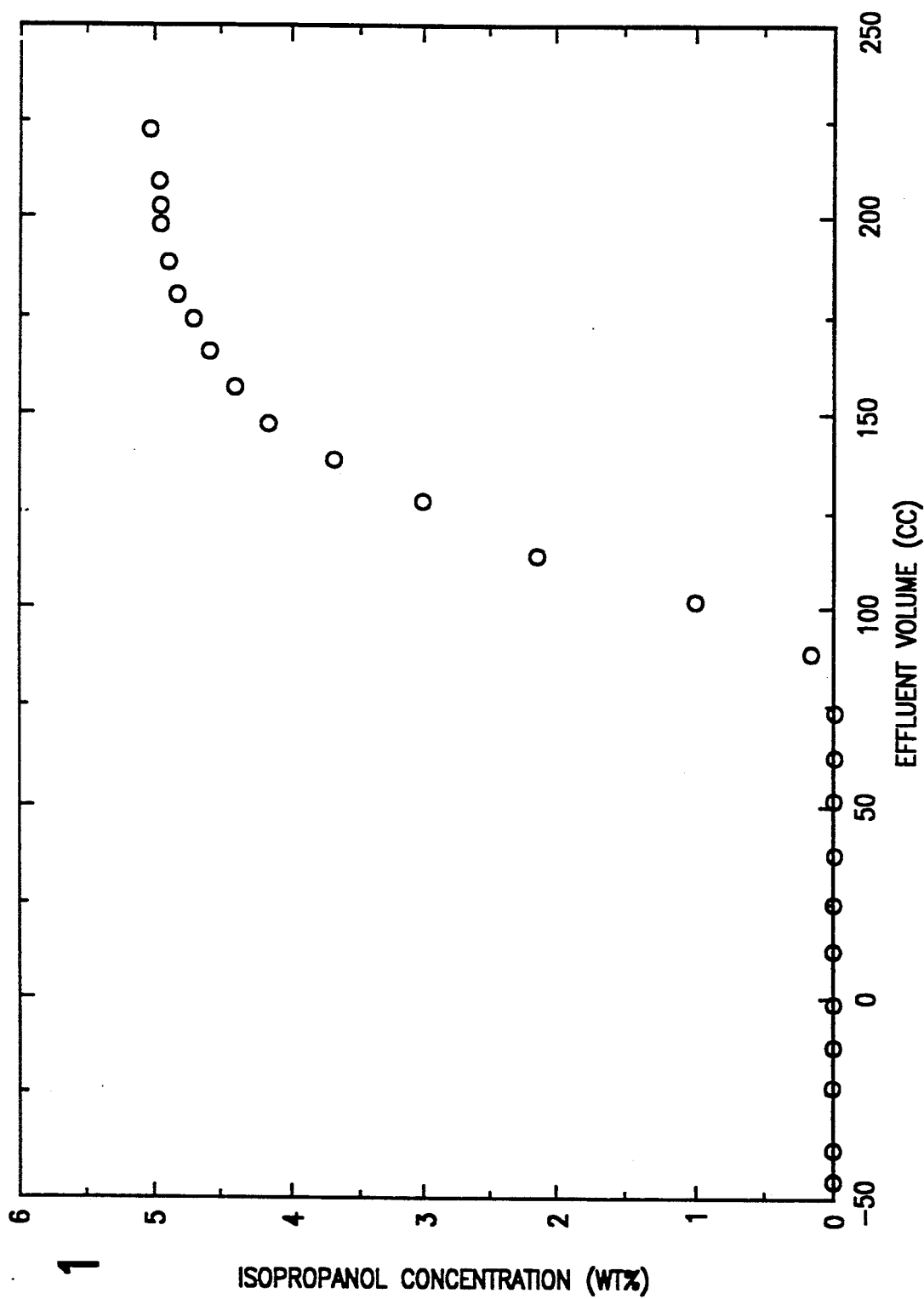
FIG. 1 shows the adsorption curve for isopropanol.

The process of this invention is useful for the separation of aromatic and aliphatic alcohols, including ethanol, isopropanol and phenol, from aqueous solutions. Zeolite Beta separates the alcohols from the aqueous streams and then concentrates them within its unique pore structure. Once trapped the captured substances may be recovered or destroyed in the zeolite.

Zeolite Beta has been found to possess high affinity for sorbing alcohols from aqueous solutions. This property can be used to effect separation of alcohols from any aqueous solution.

In an alternative embodiment, zeolite Beta can be used for the separation of alcohols in the vapor phase.

Zeolite Beta is a known zeolite which is described in U.S. Pat. Nos. 3,308,069 and Re. 28,341, incorporated herein by reference.

Zeolite Beta may be composited with a porous matrix material, such as zirconia, silica, titania, alumina, silica-alumina, silica-magnesia, silica-zirconia, silica-thoria, silica-beryllia, silica-titania as well as ternary compositions, such a silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Suitable forms of zeolite Beta for this invention include powder, granules and molded products, such as extrudates.

The separation may be conducted by contacting the aqueous alcohol-containing solution with zeolite Beta in a batch or continuous manner. The zeolite may be used in a fixed stationary bed, a fixed fluidized bed or a transport bed. More than one bed may be used in series. Alternatively, a cyclic process wherein two beds are operated in parallel may be employed.

The process is generally operated at a temperature in the range from about 50° F. to about 500° F. and preferably at a temperature of from about 50° F. to about 200° F.

The liquid hourly space velocity (LHSV) is in the range of from about 0.1 to about 10,000 hr$^{-1}$ and preferably in the range of from about 1 to about 1000 hr$^{-1}$.

The gas hourly space velocity (GHSV), defined as volume of gas/volume of sorbate per hour at 1 atmosphere and 60° F., is in the range of from about 10 to about 1,000,000 hr$^{-1}$ and preferably in the range of from about 1000 to about 10,000 hr$^{-1}$.

The contact time with zeolite Beta is as long as required to provide the desired alcohol separation. Preferably, the time is at least about 3 seconds.

Other conditions, such as pressure, are well known operating parameters and can be optimized for the process herein in the usual manner. Note, more alcohol can be adsorbed with increasing pressure.

Regeneration of zeolite sorption capacity can proceed by several alternatives with concurrent destruction or detoxification of the organic compounds. Once trapped the captured substances may be destroyed in the zeolite by a variety of techniques such as oxidation, pyrolysis, or hydroconversion with hydrogen gas. Following this, the zeolite can be regenerated for use, thereby forming the basis for a cyclic adsorption-destruction-adsorption process.

Unlike activated carbon, zeolites, such as Beta, are thermally stable. The bed can be regenerated by oxidative burning with no loss of zeolite adsorbent. The organics can be burned off in place using air or oxygen-containing mixtures without removal of adsorbent from the bed and without destruction or consumption of the adsorbent. The combustion of adsorbed organics can be enhanced by the inclusion of combustion-promoting metals, such as platinum, palladium, rhodium, nickel, cobalt, iron, manganese, chromium, vanadium, molybdenum, tungsten, sodium, potassium, magnesium, and calcium or mixtures thereof. These metals may be added to the zeolite Beta adsorbent using methods well known in the catalysis art such as impregnation, precipitation, etc., or they may be added to the adsorbent bed as separate particles.

The following examples illustrate the process of the present invention.

EXAMPLE 1

Zeolite Beta, ZSM-5, ZSM-35, and USY were compared to show the affinity of zeolite Beta for low levels of alcohol in aqueous solutions. Zeolite Beta was prepared in accordance with U.S. Pat. Nos. 3,308,069 and Re. 28,341, incorporated herein by reference. ZSM-5 and ZSM-35 were prepared in accordance with U.S. Pat. Nos. 3,702,886 and 4,016,245, respectively, which are incorporated herein by reference. USY, a commercially available catalyst, was manufactured by United Catalysts, Inc. The pure zeolite powders in the H+ form were calcined at 1000° F. for 3 hours. One gram of the zeolite solid sorbent was added to 5 cm$^3$ of an aqueous alcohol solution (2 wt. % alcohol), shaken and allowed to stand overnight in a sealed container. The sample was then centrifuged and the supernatant liquid analyzed by gas chromatography. The capacity for alcohol is calculated by mass balance on the supernatant liquid.

To gauge selectivities, competitive adsorption experiments were conducted by comparing the alcohol uptake for the 2 wt. % alcohol solution with the water uptake for a 98 wt. % alcohol-2 wt. % water solution. If a zeolite possesses high affinity for sorbing the alcohol, it will do so even in the presence of large amounts of water (98% water-2% alcohol). Likewise, when the opposite situation is presented (98% alcohol, 2% water), the zeolite should still prefer the alcohol and show a low affinity for sorbing water. Tables 1 and 2 show the competitive sorption results and selectivities for aqueous isopropanol (IPA) and ethanol (EtOH) solutions. Selectivity is defined as the uptake of alcohol, when alcohol is a minor component in the solution, divided by the uptake of water, when water is the minor component.

TABLE 1

| Zeolite Type | Uptake Minor (2 wt %) Component (mg sorbate/gm zeolite) | | Selectivity IPA/Water |
|---|---|---|---|
| | IPA | Water | |
| Beta | 113 | 22 | 5.1 |
| USY | 46 | 67 | 0.7 |
| ZSM-35 | 68 | 63 | 1.1 |
| ZSM-5 | 119 | 84 | 1.4 |

Zeolite Beta shows a high affinity for isopropanol over water. ZSM-5 shows a high capacity but only a moderate selectivity for isopropanol. Zeolite Beta shows about 5 times the affinity for isopropanol over water as compared to USY, ZSM-35 and ZSM-5.

TABLE 2

| Zeolite type | Uptake Minor (2 wt %) Component (mg sorbate/gm zeolite) | | Selectivity EtOH/Water |
|---|---|---|---|
| | EtOH | Water | |
| Beta | 28 | 36 | 0.8 |
| USY | <1 | 32 | ~0 |
| ZSM-35 | 39 | 12 | 3.3 |
| ZSM-5 | 48 | <1 | >10 |

ZSM-5 shows the highest ethanol capacity and selectivity followed by ZSM-35. Zeolite Beta shows about equal affinity for ethanol and water.

EXAMPLE 2

Adsorption breakthrough curves for isopropanol/water separation were determined by passing a 5 wt. % IPA/ 95% water solution downward through a fixed-bed contactor containing 100 cm$^3$ (60 g) of zirconia-bound zeolite Beta (70% Beta, 30% ZrO$_2$) in the form of 1/16" diameter cylindrical extrudates, at a LHSV of about 1.3. The content of IPA in the effluent was monitored by measuring the effluent density at regular intervals using a Mettler DA300 densitometer operating at 60° F.

FIG. 1 shows the adsorption curve for IPA. Almost 75 cm$^3$ of solution were passed through the bed before breakthrough was noted. In addition, the sharp adsorption front, as evidenced by the rapid increase in IPA concentration after breakthrough, indicates strong, preferential adsorption. FIG. 2 shows the breakthrough curve for desorption of IPA from the bed by elution with 100% water. The early breakthrough of water and slow increase in water concentration with effluent volume again indicates that IPA is preferentially bound to the zeolite.

EXAMPLE 3

This example demonstrates the affinity of zeolite Beta for phenol. Zeolite Beta, as well as ZSM-5, ZSM-35, and USY (prepared according to the method of Example 1) were tested by contacting 1 gram of zeolite powder with 5 cm$^3$ of a 2 wt. % phenol solution. The amount of phenol in the supernatant liquid after contact overnight was measured by gas chromatography and the amount of phenol adsorbed per gram of zeolite was calculated. The data are shown in Table 3. Each zeolite shows a positive affinity for phenol, as evidenced by an uptake of organic, but differ in their capacities for adsorption. Zeolite Beta shows the highest uptake, about 68 mg phenol adsorbed per gram. Zeolite Beta sorbs about 3.2 times more phenol than USY and about 1.7 times more phenol than ZSM-5.

TABLE 3

| Zeolite Type | Si/Al$_2$ Ratio* | Phenol Uptake mg Phenol/gm Zeolite |
|---|---|---|
| Beta | 50 | 68 |
| USY | 5–50 | 21 |
| ZSM-5 | 55 | 39 |
| ZSM-35 | 18–35 | 12 |

*Approximate values

EXAMPLE 4

The ability of zeolite Beta to sorb alcohols from the vapor phase is demonstrated by contacting the zeolite with an alcohol-containing vapor stream and measuring the uptake gravimetrically. Experiments were conducted in a DuPont Model 950 thermogravimetric analyzer (TGA) equipped with a gas manifold and thermostated vaporizer for flowing various gas mixtures over the sample. Zeolite Beta powder was loaded onto the sample pan and calcined in air at 1000° F. to remove any previously adsorbed substances. The sample was then cooled to 212° F. and a helium stream containing 8 volume percent isopropanol was passed over the sample while monitoring weight gain in the TGA. Within one hour, the sample weight gain had equilibrated and the sorption of isopropanol was found to be 141 mg/gram of zeolite Beta. The adsorbed isopropanol was completely removed by heating the sample above 500° F. in the TGA. These results demonstrate that zeolite Beta can sorb alcohols from the vapor phase and that the alcohol can be removed by heating. Thus, the zeolite can be used for multiple sorption-desorption cycles.

These results demonstrate that zeolite Beta is most effective for separating alcohols containing 3 or more carbon atoms, for example from 3 to about 30 carbon atoms.

The process of this invention is especially useful in processes which employ chemical separation and wastewater treatment. Zeolite Beta can be used as a selective sorbent for isopropanol in olefin hydration and in two stage propylene to di-isopropyl ether synthesis (DIPE). The ability to separate alcohol from water is beneficial in cases where dry alcohol feedstock is needed to promote olefin-alcohol etherification and to minimize competing olefin hydration reactions. Zeolite Beta sorbents can further be used in the DIPE process and in IPA synthesis as traps to remove alcohol from wastewater prior to discharge into the plant's regular treatment facility.

The sorption properties of zeolite Beta for phenol may also be used for the cleanup of process streams that contain phenol or are a byproduct of phenol production. Examples include the aqueous stream discharged by a refinery crude desalter unit, leachate from coal processing, leachate from landfills, and chemical plant wastewaters.

Another advantage of the process of this invention is that the thermal stability of zeolites such as zeolite Beta permits the in-situ destruction of adsorbed organics by oxidation.

Changes and modifications in the specifically described embodiments can be carried out without departing from the scope of the invention which is intended to be limited only by the scope of the appended claims.

What is claimed is:

1. A process for the separation of alcohol from an aqueous alcohol-containing solution comprising contacting the aqueous alcohol-containing solution with a composition comprising zeolite Beta for a sufficient time to sorb said alcohol.

2. The process of claim 1 wherein said alcohol has 3 or more carbon atoms.

3. The process of claim 1 wherein said alcohol is aliphatic, aromatic or a mixture thereof.

4. The process of claim 1 wherein said alcohol comprises isopropanol.

5. The process of claim 1 wherein said alcohol comprises phenol.

6. The process of claim 1 wherein said composition comprising zeolite Beta is regenerated by oxidative burning.

7. The process of claim 1 wherein said composition comprising zeolite Beta is regenerated by contact with hydrogen gas.

8. The process of claim 1 wherein said aqueous alcohol-containing solution is wastewater.

9. The process of claim 1 wherein said composition comprising zeolite Beta further comprises a combustion-promoting metal.

10. The process of claim 1 wherein said contacting is at a temperature in the range of from about 50° F. to about 500° F.

11. The process of claim 1 wherein said contacting is at a liquid hourly space velocity in the range of from about 0.1 to about 10,000.

12. A process for the separation of isopropanol from an aqueous isopropanol-containing solution comprising contacting the aqueous solution with a composition comprising zeolite Beta for a sufficient time to sorb said isopropanol.

13. A process for the separation of alcohol from an alcohol-containing vapor stream comprising contacting said alcohol-containing vapor stream with a composition comprising zeolite Beta for a sufficient time to sorb said alcohol.

14. The process of claim 13 wherein said alcohol has 3 or more carbon atoms.

15. The process of claim 13 wherein said composition comprising zeolite Beta is regenerated by oxidative burning.

16. The process of claim 13 wherein said composition comprising zeolite Beta is regenerated by contact with hydrogen gas.

17. The process of claim 13 wherein said composition comprising zeolite Beta further comprises a combustion-promoting metal.

18. The process of claim 13 wherein said contacting is at a gas hourly space velocity in the range of from about 10 to about 1,000,000.

* * * * *